United States Patent [19]

Sramek

[11] Patent Number: 4,677,984
[45] Date of Patent: Jul. 7, 1987

[54] CALIBRATED ARTERIAL PRESSURE MEASUREMENT DEVICE

[75] Inventor: Bohumir Sramek, Irvine, Calif.

[73] Assignee: Bomed Medical Manufacturing, Ltd., Irvine, Calif.

[21] Appl. No.: 653,460

[22] Filed: Sep. 24, 1984

[51] Int. Cl.[4] ............................................. A61B 5/02
[52] U.S. Cl. ................................... 128/681; 128/700; 128/708; 128/679
[58] Field of Search ................ 128/672, 677, 680–683, 128/679, 686, 700, 708

[56] References Cited

U.S. PATENT DOCUMENTS

| 3,149,628 | 9/1964 | Bolie | 128/680 |
| 3,280,817 | 10/1966 | Jorgensen et al. | 128/700 |
| 3,348,534 | 10/1967 | Marx et al. | 128/679 |
| 3,779,235 | 12/1973 | Murphy | 128/682 |
| 3,878,833 | 4/1975 | Arneson et al. | 128/672 |
| 3,885,551 | 5/1975 | Massie | 128/682 |
| 4,058,117 | 11/1977 | Kaspari et al. | 128/682 |
| 4,211,238 | 7/1980 | Shu | 128/700 |
| 4,216,779 | 8/1980 | Squires | 128/682 |
| 4,343,314 | 8/1982 | Sramek | 128/680 |
| 4,408,614 | 10/1983 | Weaver | 128/680 |
| 4,425,922 | 1/1984 | Conti | 128/691 |
| 4,446,872 | 5/1984 | Marsoner | 128/700 |
| 4,549,552 | 10/1985 | Groch et al. | 128/700 |

FOREIGN PATENT DOCUMENTS

| 0021800 | 1/1981 | European Pat. Off. | 128/800 |
| 0869754 | 10/1981 | U.S.S.R. | 128/680 |

Primary Examiner—Kyle L. Howell
Assistant Examiner—Angela D. Sykes
Attorney, Agent, or Firm—Knobbe, Martens, Olson & Bear

[57] ABSTRACT

An apparatus and method are disclosed for measuring and recording the arterial blood pressure waveform or a portion thereof in a patient by detecting the momentary increases in pressure in an occlusive cuff caused by the passage of blood through an artery beneath the cuff. The magnitudes and times at which the momentary pressure increases occur and disappear with respect to the R-wave in an electrocardiograph signal are recorded as the pneumatic pressure applied to the cuff is gradually increased or decreased. The sampled times and magnitudes are processed to accurately reproduce the arterial blood pressure waveform of the patient. The apparatus includes an improved pressure cuff having a separate occlusive bladder and a sensing bladder to increase the accuracy of the pressure measurements.

21 Claims, 22 Drawing Figures

PRIOR ART

PRIOR ART

| TIME | PRESSURE |
|---|---|
| T(R1-B1) | PB1 |
| T(R1-N1) | PN1 |
| T(R2-B2) | PB2 |
| T(R2-N2) | PN2 |
| T(R2-B2') | PB2' |
| T(R2-N2') | PN2' |
| T(R3-B3) | PB3 |
| T(R3-N3) | PN3 |
| T(R4-B4) | PB4 |
| T(R4-N4) | PN4 |
| T(R5-B5) | PB5 |
| T(R5-N5) | PN5 |
| T(R6-B6) | PB6 |
| T(R6-N6) | PN6 |
| T(R7-B7) | PB7 |

CALIBRATED ARTERIAL PRESSURE MEASUREMENT DEVICE

BACKGROUND OF THE INVENTION

1. Field of the Invention

The present invention provides an apparatus and a method for measuring and recording the blood pressure waveform of a patient by detecting momentary increases in the pressure of an occlusive blood pressure cuff, and recording the time and magnitude at which the pressure increases appear and disappear with respect to the R-wave of an electrocardiograph signal.

2. Prior Art

Currently used non-invasive techniques for determining the arterial blood pressure use the sphygnomanometric principle. This familiar blood pressure measuring technique generally comprises the steps of placing the occlusive cuff around the brachial portion of the arm and rapidly inflating it to a pressure substantially higher than the expected systolic pressure level. At this point, both the arterial and the venous flow to the arm distal to the cuff are occluded. Both the artery and the vein under the cuff are collapsed since the external pressure, transferred from the cuff by the tissue, is higher than the intra-vessel pressure. Typically, the maximum (systolic) arterial blood pressure at this point is 120 torr (mm of mercury), the diastolic (minimum) pressure is 80 torr, and the pressure of the returning venous blood is 15 torr. Thus, the cuff is inflated to a pressure in excess of 120 torr for a typical normotensive patient.

The cuff pressure is then slowly decreased until it reaches a point at which the peak arterial pressure is slightly higher than the occlusive cuff pressure. At this point, the intra-arterial pressure overcomes the external pressure, the artery expands, and a bolus of blood is pushed through the artery into the distal portion of the arm. The artery at this point is severely pinched; therefore, the resulting momentary flow is turbulent (normal flow is laminar) giving rise to Korotkoff sounds heard by a stethoscope placed on the brachial artery below the cuff. The pressure at which the first appearance of Korotkoff sounds is detected is generally denominated as the systolic pressure level.

As the cuff is slowly further deflated, the ratio of the time in which the arterial pressure is higher than the cuff pressure to the time in which the artery is occluded increases. As the pinching of the artery becomes less severe, the flow is less turbulent, and the Korotkoff sounds, although longer in duration, are less pronounced until they completely disappear. At this point, the artery is substantially fully expanded and the arterial flow is laminar. The pressure at this point is generally denominated as the diastolic pressure level.

Since the brachial vein is still collapsed at cuff pressures below the diastolic pressures and above the venous blood pressure, the flow to that portion of the arm distal to the cuff results in blood pooling, felt by the patient as a discomfort or pain. The venous pool will not be released until the cuff pressure falls below the venous pressure level. For that reason, when there is an assurance that the diastolic pressure level has been passed, the cuff is rapidly deflated to minimize the discomfort to the patient.

The auscultatory method described above has built-in limitations of accuracy since it depends upon a human operator. For instance, the person performing the blood pressure check may fail to hear or recognize the auditory changes associated with the two pressure levels. Furthermore, the blood pressure may be decreased too rapidly to obtain an accurate reading of pressure at which the sounds change.

The need to reduce the human error in obtaining blood pressure measurements, and the need for automatic periodic monitoring of blood pressure has resulted in the development of semiautomatic and fully automatic blood pressure measurement systems. Generally, these systems essentially emulate the above-described method of measurement. The difference is typically in the method of detecting the systolic and diastolic pressure levels. In one prior method, a microphone is built into the cuff and replaces the stethoscope used by the physician or other person performing the measurement. An electronic device connected to the microphone will detect the appearances and disappearances of the Korotkoff cuff sounds and correlate them with the cuff pressure when the changes are detected. The accuracy of this method will be limited by the ability of the electronic circuitry to discriminate between the turbulent blood flow and any other sounds that may be present. In many instances, the tests are performed in a soundproof room to eliminate extraneous noise and obtain a desired degree of accuracy. Furthermore, the apparatus requires an electrical connection between the cuff and the system in addition to the pneumatic connection to supply pneumatic pressure to the cuff.

Another method developed is the use of two pressure transducers placed at the beginning and end of the occlusive cuff. The two transducers detect the differential pressure caused by the propagating bolus of blood and therefore can detect the beginning of turbulent blood flow. Again, an electrical connection is required to connect the pressure transducers to the monitoring system.

One of the simplest fully automated methods of detecting blood pressure is the oscillometric method. The oscillometric method only requires one transducer, which can be located at the system end of the pneumatic connection between the cuff and the system. Thus, no electrical connections are required between the patient and the system. The oscillometric method detects the momentary increases in cuff pressure caused by the passage of a bolus of blood through the artery beneath the cuff. The momentary expansion of the artery results in an increase in the volume of the tissue under the cuff and is reflected in a momentary increase of the cuff pressure. As the cuff pressure becomes lower, the volume of the bolus of blood is higher and the momentary increase of the cuff pressure is higher.

The amplitude of the pressure pulses reflected back into the cuff pressure increase to a point at which the mean pressure level is reached. From this point, their magnitude will progressively decrease until the diastolic pressure level is passed, from which level they will stay at a constant amplitude level dictated by the arterial pressure compliance. The first appearance of the cuff pressure pulses defines the systolic pressure level, the maximum amplitude of the pulses corresponds to the mean arterial pressure level, and the last measurable decrease of the amplitude of the cuff pressure pulses signifies the diastolic pressure level.

The oscillometric method has a number of drawbacks including the fact that only the systolic, diastolic and mean pressure levels can be determined. More importantly, the shape of the arterial pressure waveform, which has significant diagnostic and clinical meaning, is unknown. The maximum rate of systolic pressure change, an indicator of the heart's contractility, cannot be determined. Finally, there is no verification that measured arterial pressure levels are correct since the transducer is attempting to measure a transient pressure level.

The accuracy of the pressure measurement is indirectly proportional to the rate of deflation of the cuff. An increase in accuracy obtained by reducing the deflation rate results in a corresponding increase in the pain and discomfort to the patient because of blood pooling. Thus, there is a need for an automated blood pressure measurement method and device to increase the accuracy of the measurements, to provide more diagnostic and clinical information, and to reduce the pain and discomfort to the patient.

SUMMARY OF THE INVENTION

The apparatus and method of the present invention non-invasively measure and record the arterial blood pressure waveform with sufficient accuracy that the waveform or a portion thereof can be reconstructed and displayed. The method is independent of whether linear or step cuff inflation or deflation is used. Additional information about the heart's contractility can be derived from the reconstructed arterial waveform. The displayed arterial waveform can be examined for any discrepancies to immediately indicate whether a test is invalid for reasons of artifact signals or other reasons.

The apparatus and method can be used to reconstruct the arterial pressure waveform either during deflation or during inflation of the cuff. Thus, the cuff inflation process can be stopped at the point when the systolic pressure has been reached and the cuff deflated immediately. This feature reduces both the time required for making the measurement and the discomfort to the patient. The rate of inflation or deflation of the cuff within the active pressure range (between the systolic and diastolic pressure levels) can be controlled manually or automatically to produce needed density of sampling and display points for satisfactory results.

The invention can utilize an ordinary occlusive cuff with a pressure transducer connected to the pneumatic pressure supply. The apparatus detects the momentary increases in pressure corresponding to the passage of the bolus of blood beneath the cuff, as described for the prior art systems. Rather than detecting the magnitude of the pressure increases, the apparatus measures the time of appearance of the increase in cuff pressure with respect to the R-wave of an electrocardiograph signal, and, similarly, detects the time of the disappearance of the momentary increase. The cuff pressure at each of these points is measured and recorded. The times of the appearances and disappearances can be measured and recorded as the cuff pressure is increased or as it is decreased. At the completion of the test procedure, the recorded data points are available to accurately reproduce the pressure waveform and to provide clinical and diagnostic information such as maximum rate of pressure change.

A preferred embodiment of the invention includes an improved pressure cuff comprising an occlusive bladder for exerting pressure on the artery and a sensing bladder for detecting the flow of blood when the arterial pressure exceeds the pressure of the occlusive bladder. The improved cuff further increases the accuracy of the disclosed invention.

DETAILED DESCRIPTION OF THE DRAWINGS

Figure 1:
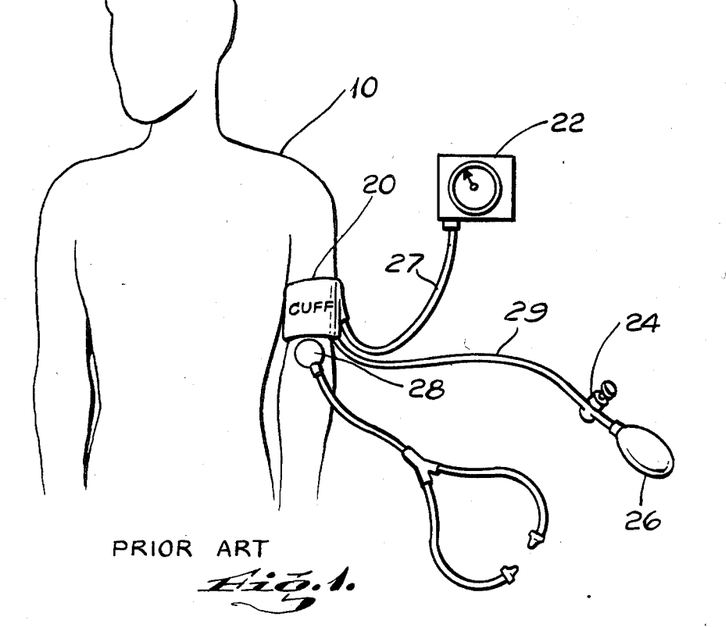
FIG. 1 illustrates a typical prior art system for measuring blood pressure.

FIG. 1 illustrates a typical prior art method of determining blood pressure by physicians or other medical personnel. An inflatable cuff 20 is applied to the upper arm of a patient 10. The cuff 20 is connected by an air hose 27 to a pressure indicator 22 and by a hose 29 to an inflation device 26, which is typically a hand-operated ball pump. The ball pump 26 is squeezed repeatedly, forcing air into the cuff 20 until the pressure, as indicated by the indicator 22, is sufficient to occlude the flow of blood through the brachial artery beneath the cuff 20. Typically, the cuff 20 is inflated to a substantially higher pressure than the expected systolic blood pressure. For example, if the systolic pressure is expected to be 120 torr, the cuff 20 will be inflated to 150 torr, or more, to assure that the brachial artery is fully collapsed.

The pick-up portion of a stethoscope 28 is placed on the arm below the cuff 20 in a position to detect the sound of blood through the brachial artery. The pressure in the cuff 20 is slowly released by allowing air to escape through a release valve 24. The physician or other person checking the blood pressure listens for the Korotkoff sounds caused when the first bolus of blood passes through the brachial artery beneath the cuff. The pressure indicated on the the pressure indicator 22 at this time is denominated as the systolic blood pressure. The Korotkoff sounds will continue as long as the artery is significantly pinched by the pressure in the cuff. When the Korotkoff sounds are no longer heard, the diastolic arterial pressure is substantially equal to or greater than the cuff pressure, and laminar flow of blood through the artery has resumed throughout the cardiac cycle. The pressure indication on the pressure indicator 22 at this point is denominated as the diastolic blood pressure.

Figure 2A:
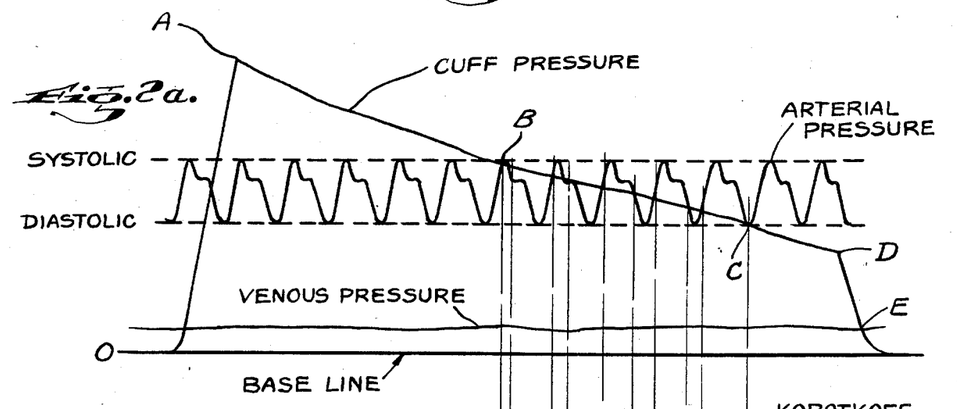
FIG. 2a and FIG. 2b illustrate the relationship between the slowly decreasing cuff pressure and the detected Korotkoff sounds.
Figure 2B:
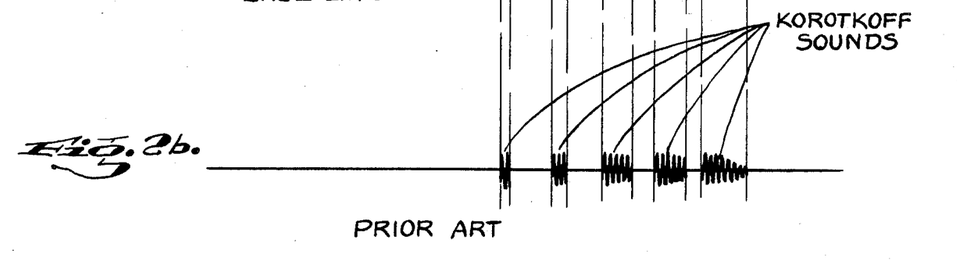

The foregoing description of the manual technique for determining blood pressure is illustrated graphically in FIGS. 2a and 2b. The arterial pressure, illustrated in FIG. 2a, varies periodically between its minimum amount, the diastolic blood pressure, and its maximum amount, the systolic blood pressure. Typical values for the pressure are 80 torr for the diastolic pressure and 120 torr for the systolic blood pessure. The venous blood pressure, also illustrated in FIG. 2a, is typically much lower than the arterial blood pressure, with 15 torr being an approximate magnitude. As shown in FIG. 2a, the cuff 20 (FIG. 1) is rapidly inflated until the cuff pressure greatly exceeds the expected systolic blood pressure. At that point, illustrated as point A, the cuff pressure is gradually reduced while listening for the Korotkoff sounds with the stethoscope. When the cuff pressure decreases to the systolic blood pressure, illustrated as point B, the arterial blood pressure will momentarily exceed the cuff pressure and a bolus of blood will pass through the artery beneath the cuff 20. This will be detected by the physician or other examiner as a momentary sound caused by the turbulent flow of the blood through the artery as illustrated in FIG. 2b. As the cuff pressure continues to decrease, the duration and the pitch of the Korotkoff sound will change as the arterial pressure exceeds the cuff pressure for increasing portions of the heart cycle. At the same time, the blood flow becomes less turbulent and more laminar, thus decreasing the loudness of the Korotkoff sounds. Finally, at point C, the cuff pressure is less than the arterial pressure throughout the entire heart cycle. At this point, laminar flow occurs throughout the heart cycle, and the Korotkoff sounds are no longer heard, as illustrated in FIG. 2b. After the Korotkoff sounds disappear, the cuff is rapidly deflated as shown by the pressure line from point D to point E. Until the cuff pressure decreases below the venous pressure at point E, the blood will continue to collect in the veins since the veins are constricted by the cuff pressure. If the cuff pressure is not released rapidly, this venous pooling will cause discomfort and pain to the patient.

It can be readily appreciated that the accuracy of the above-described method of determining blood pressure is highly subjective. If the cuff pressure is reduced too rapidly, the initial Korotkoff sounds, corresponding to the systolic blood pressure, may not be detected. Similarly, the diastolic blood pressure may be inaccurately determined. The accuracy of the reading is also very dependent upon the ability of the examiner to detect the first short duration Korotkoff sounds when the cuff pressure is near the systolic blood pressure level, and the last low intensity Korotkoff sounds when the cuff pressure is near the diastolic blood pressure level.

A typical automated auscultatory blood pressure checking device substitutes electrical devices such as a microphone and an automatic pressure recording system for the ears and eyes of the examining person. However, such devices suffer from many of the same inaccuracies associated with the manual method, that of being able to accurately distinguish the Korotkoff sounds from other noise. Furthermore, the devices are unable to provide information regarding the actual blood pressure waveform other than the maximum and minimum pressure levels.

The Present Invention

Figure 3:
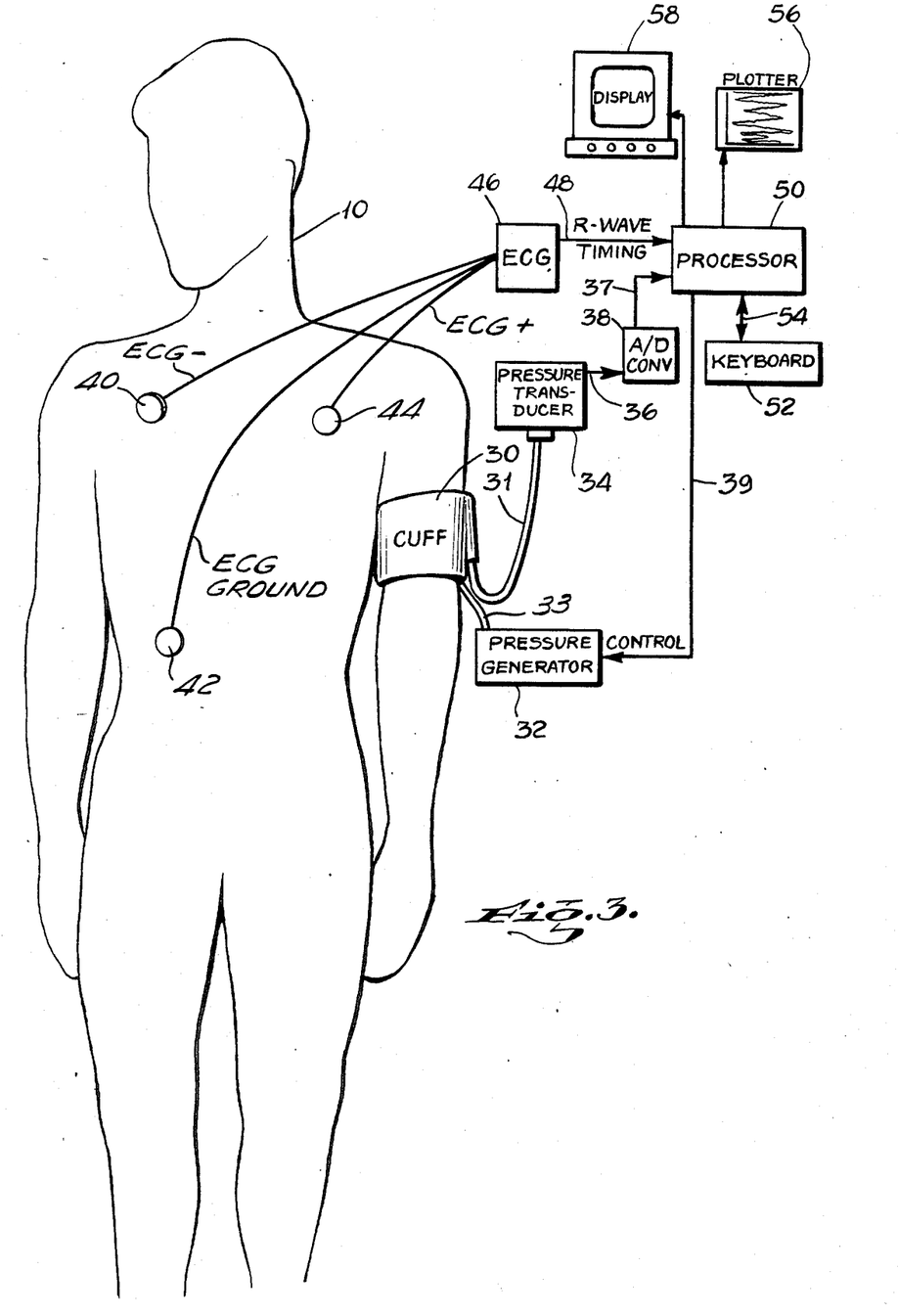
FIG. 3 illustrates the blood pressure measuring system of the present invention.

FIG. 3 illustrates the apparatus of the present invention. A cuff 30, similar to the cuff 20 of FIG. 1, is attached to the upper arm of a patient 10 in the manner previously described. The pneumatic pressure, typically air, is provided by a pressure generator 32 through a pneumatic line 33 to the cuff 30. Typically, the pressure generator 32 will comprise an electrically operated pump and an electrically operated bleeder valve (not shown). Other embodiments can include a replaceable pressurized canister or a centralized source of air pressure.

A pressure transducer 34 is connected to the cuff 30 via line 31 such that it can detect and measure the pressure in the cuff 30. The pressure transducer 34 provides a signal output on an electrical signal line 36 corresponding to the magnitude of the measured pressure. The line 36 is connected to an analog-to-digital converter 38 which converts the analog signal from the pressure transducer 34 to a digital representation of the pressure.

The digital signal is transmitted by an electrical signal line 37 to a control means such as a processor 50. Typically, the processor 50 is a microprocessor having a code memory programmed to cause the microprocessor to input data from external signal sources, such as the analog-to-digital converter 38, and execute software algorithms to analyze the data and generate output data. The processor 50, has data storage memory for storing the data which are input. The processor 50 generates control signals which are transmitted by an electrical signal line 39 to the pressure generator 32. The control signals on the line 39 operate flow valves (not shown) within the pressure generator 32 to increase and decrease the pneumatic pressure applied to the cuff 20 through the pneumatic line 33 at controlled variable rates.

Figure 4A:
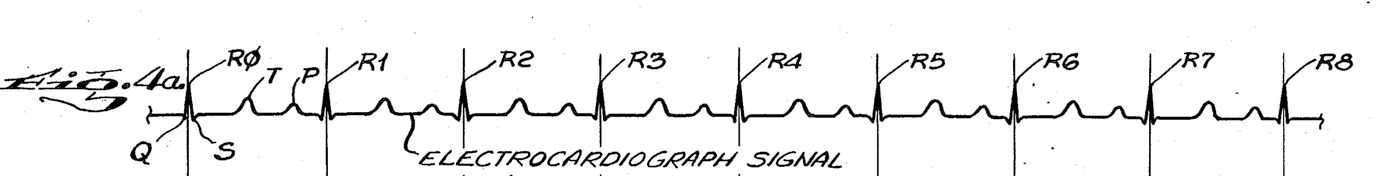
FIG. 4a and 4b illustrate the relationship between the electrocardiograph signals, the blood pressure and the cuff pressure as the measurements are taken by the system of FIG. 3.

The processor 50 also receives inputs from an electrocardiograph device 46, which is connected to the patient 10 by ECG— electrode 40, ECG ground electrode 42, and ECG+ electrode 44. Typically, the electrodes 40, 42, and 44 are connected to the regions roughly corresponding to the right arm, the right leg, and the left arm of the patient 10, respectively, in order to detect the electrical activity of the patient's heart. A typical electrocardiograph signal is illustrated in FIG. 4a. As shown, the R-waves in the electrocardiograph signal are detectable as the signals having the greatest magnitude in each cycle of the electrocardiograph and are illustrated as R0–R8. The occurrence of the R-wave corresponds to the beginning of ventricular contraction as it is the peak of the depolarization wave which triggers ventricular contraction. Returning to FIG. 3, the electrocardiograph device 46 provides an output signal corresponding to the occurrence of the R-wave in each heart cycle. This R-wave timing is provided to the processor 50 by an electrical signal line 48 and is used to time the sampling of the blood pressure by the processor 50 in a method to be described below.

Typically, the processor 50 can be a microprocessor and its associated memory, timing and interface components. The processor 50 is programmed to respond to data and timing signals from the pressure transducer 34 and electrocardiograph device 46, and generate signals to the pressure generator 32 to control the increases and decreases in pressure applied to the cuff 20. The processor 50 is programmable in a conventional manner to apply the control signals to the pressure generator 32 in sequences such that the pressure is applied to and released from the cuff 30 at controlled rates, as will be described below. The processor 50 applies software implemented algorithms to the data from the transducer 34 and electrocardiograph device 46 to provide output signals which provide information regarding the magnitudes of the arterial pressure and the shape of the pressure waveform, according to a method described below.

A typical blood pressure system also includes a keyboard 52, connected to the processor 50 by interconnection lines 54, to enable the person performing the examination to manually control the processor 50. The system may also include a display 58 and a plotter 56 for displaying the blood pressure information and for displaying and plotting the reproduced blood pressure waveform and which are connected to the processor 50 in conventional manners.

Method of Determining Blood Pressure

Figure 4B:
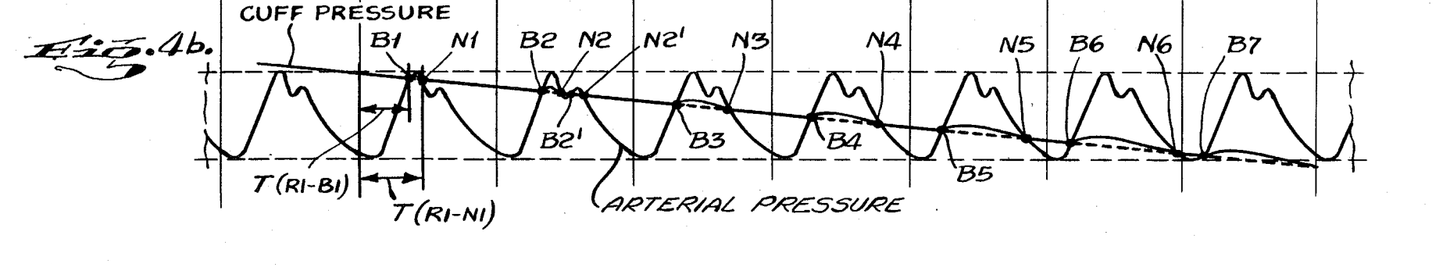

FIGS. 4a and 4b illustrate the relationship between the electrocardiograph signal and the blood pressure waveform, respectively. The R-waves of the electrocardiograph signal, designated as R0–R8 in FIG. 4a, are used as reference points since they are detectable as the greatest amplitude of the electrical signal. The R-wave in each cycle results from the electrical depolarization of the heart muscle and triggers the ventricular contraction which causes the arterial blood flow in each cycle. Each pressure measurement is timed with respect to the most recent occurrence of an R-wave synchronization signal.

Also illustrated in FIG. 4b is a graph of the cuff pressure, superimposed upon the graph of the arterial blood pressure waveform. As illustrated, the cuff pressure is initially higher than the systolic blood pressure and decreases to a point lower than the systolic blood pressure. For instance, in the period between the R-wave, R0, and the R-wave, R1, the cuff pressure is greater than the systolic blood pressure. Between the R-wave, R1, and the R-wave, R2, the systolic peak of the blood pressure waveform exceeds the cuff pressure for a short duration. During this time, between the points B1 and N1 on the cuff pressure graphs, the bolus of blood passes through the brachial artery beneath the cuff. The pressure caused by the bolus of blood is transmitted through the tissues of the arm to the cuff causing the cuff pressure to increase slightly above the expected cuff pressure. (The expected cuff pressure is illustrated in dashed lines in FIG. 4b.) The transducer 34 and the analog-to-digital converter 38 (FIG. 3) have sufficient sensitivity to detect the momentary increase and subsequent decrease in cuff pressure caused by the passage of the bolus of blood. The processor 50 (FIG. 3) records the pressure at which each abrupt transition occurs and the time elapsed since the occurrence of the last R-wave synchronization signal from the electrocardiograph device 46 (FIG. 3). Typically, the elapsed time and the pressure are stored in the electronic memory of the processor 50 as pairs of data values.

In one embodiment of the invention, the processor 50 continually monitors the decreasing cuff pressure. At the same time, the processor 50 transmits commands to the pressure generator 32 to cause the generator 32 to decrease the pressure in the cuff 30 at a steady, known rate. In the absence of arterial blood pressure in excess of the cuff pressure, the cuff pressure decreases at this steady, known rate, and the output of the pressure transducer 34 through the analog-to-digital converter 38 will also steadily decrease. Thus, the detected pressure is coincident with the expected or known pressure. At the point designated B1, the detected blood pressure abruptly increases above the expected magnitude. The processor 50 detects this abrupt increase in the output of the transducer 34 through the analog-to-digital converter 38 and executes an internal software routine to store the expected magnitude of the pressure (i.e., the magnitude of the pressure if the abrupt increase had not occurred), and also to store the elapsed time at which the abrupt change was detected with respect to the most recent R-wave, in this case, R1. Typically, the elapsed time is determined by an internal counter which is reset with the occurrence of each R-wave and is incremented periodically by the occurrence of an internal timing signal. In FIG. 4b, the elapsed time from the R-wave, R1, to B1, the detected transition above the expected cuff pressure, is shown as T(R1-B1). The elapsed times to the other pressure increase transition points are not shown.

The processor 50 continues to monitor the detected pressure and calculate the expected pressure using the known rate of decrease and the elapsed time as factors for the calculation. When the detected cuff pressure again returns to the expected value, that value is recorded along with the elapsed time. The first such occurrence is designated as N1 in FIG. 4b. The FIG. 4b, the elapsed time from the R-wave, R1, to N1, the detected transition back to the expected cuff pressure, is shown as T(R1-N1). The processor 50 does not have to measure the actual value of the blood pressure during the momentary increase since the value recorded is the expected value of the cuff pressure rather than the measured value.

As the cuff pressure decreases further, the departures from and the returns to the expected cuff pressures occur at lower pressures. These points are designated as B2-B7 and N2-N6, respectively, in FIG. 4b. Each transition will be stored in the memory of the processor 50 as a pressure magnitude and an elapsed time from the most recent R-wave.

Typically, one abrupt increase above and one return to the expected cuff pressure occur during each heart cycle. However, as illustrated in the heart cycle bounded by the R-wave, R2, and the R-wave, R3, two additional transitions, e.g. B2' and N2', can occur during some cardiac cycles. These multiple transitions occur because the blood pressure waveform is a complex curve, such as is illustrated for the dicrotic notch, rather than a simple smooth curve. Thus, the apparatus and method described herein must accommodate multiple transitions in order to accurately reproduce the waveform. This is accomplished by determining the time elapsed from the last detected R-wave to each abrupt transition in the cuff pressure. The internal elapsed time counter in the processor 50 is reset only upon the occurrence of an R-wave; thus, the pressure at additional transitions within the same cycle are simply stored along with the elapsed time at which they occur relative to the most recent R-wave. Thus, the processor 50 will store data corresponding to the pressure magnitudes and elapsed times for points B2, N2, B2' and N2'. Each of the elapsed times, T(R2-B2), T(R2-N2), T(R2-B2') and T(R2-N2'), (not shown on FIG. 4b) are measured from the R-wave, R2.

In the heart interval bounded by the R-wave, R7, and the R-wave, R8, the processor 50 will detect the increased cuff pressure, designated as B7. However, there is no corresponding return to the expected cuff pressure. Thus, the processor 50 will designate the expected cuff pressure at the last transition, B7, as the diastolic blood pressure, in addition to recording the elapsed time and pressure. If at least one R-wave to R-wave cycle occurs without a transition in the cuff pressure, the processor 50 will conclude the sampling portion of the measurement.

Figure 5:
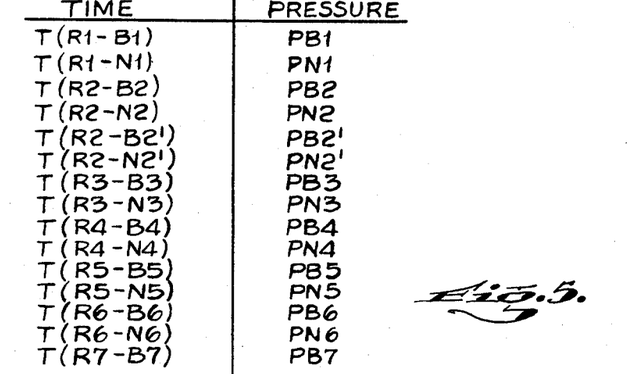
FIG. 5 illustrates a table of data points taken from the measurements of FIGS. 4a and 4b.

At the conclusion of the sampling portion of the examination, the processor 50 will have stored in its memory a number of pairs of sampled data, corresponding to the transition points. This is illustrated by means of a table in FIG. 5. As set forth above, each time, e.g., T(R1-B1), corresponds to the elapsed time from the last R-wave to the pressure transition, and each pressure corresponds to the expected cuff pressure at the transition. The actual method of storage in the processor 30 memory will of course depend upon the chosen data format in the processor 50.

Figure 6:
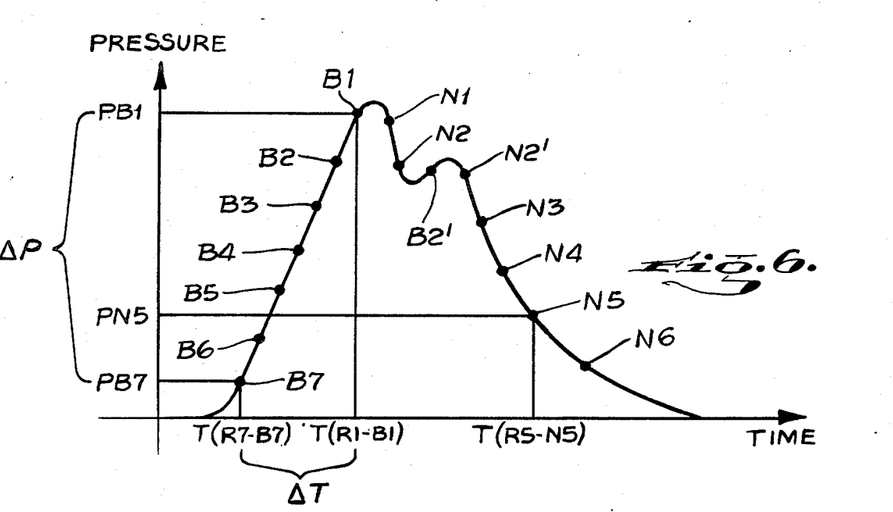
FIG. 6 illustrates the reproduced blood pressure waveform from the data points obtained in accordance with FIGS. 4a and 4b.

FIG. 6 illustrates how the sampled points, measured as described above in connection with FIGS. 4a and 4b, are used to reproduce the pressure waveform. The horizontal axis of the plot is the elapsed time from the R-waves to the sampled points. The vertical axis is the pressure measured at the transition points. For example, the time, T(R1-B1), corresponds to the time from the R-wave, R1, to the transition point B1; and the pressure, PB1, corresponds to the cuff pressure measured when the transition occurred. Similarly, the time, T(R5-N5), and the pressure, PN5, correspond to the time and pressure for the point N5. Typicallly, the data points are plotted on a paper plotter or on a video display screen, such as those illustrated in FIG. 3, to provide a reproduction of the pressure waveform similar to the illustration in FIG. 6.

Typically, a smoothing algorithm will be applied to the data points to determine the nature of the waveform between the plotted points. For example, it is clear that the waveform between the points B1 and N1 is not a straight line. An algorithm can be used to approximate a curve between the two points to more accurately determine the systolic blood pressure. Thus, it is not necessary that a pressure sample be taken at the peak of the waveform. The waveform illustrated is shown after a typical smoothing algorithm has been applied to the data points to interconnect the points with smooth curves rather than straight lines.

In addition to providing a display of the waveform, the processor 50 can analyze the data by applying one or more well known computer algorithms to the data points stored in memory to provide useful output information concerning the waveform. For example, the slope of the pressure waveform between the points B7 and B1 in FIG. 6 (i.e., $\Delta P/\Delta T = PB1-PB7 \sim T(R1-B1)-T(R7-B7)$) provides significant clinical information regarding the contractility of the heart. The contractility of the heart is the rate at which the heart muscle can contract and propel the blood from the ventricles. This is an important measure of the ability of the heart to respond to the demands of exercise since the heart must be able to rapidly expel the ventricular blood in order to increase the rate of blood flow. The contractility of the heart can be determined from the data points by performing the calculation above and can be provided as an output independent of the reproduced waveform. The contractility of the heart is proportional to the rate of increase in the arterial blood pressure with respect to time.

Alternative algorithms can be applied to the data points to calculate the mean arterial blood pressure, another important indicator of the relative health of the patient's heart.

As can now be seen, the apparatus and method of the present invention provide a substantial improvement over the prior art. In addition to determining the systolic and diastolic blood pressures by detecting the first and last occurrence of transitions in the cuff pressure, the invention produces a blood pressure waveform which can be analyzed to verify the accuracy of the measured pressures. Furthermore, the pressure waveform can be analyzed to detect abnormalities in the blood flow which may not be detected by simply measuring the maximum and minimum blood pressures.

Figure 7A:
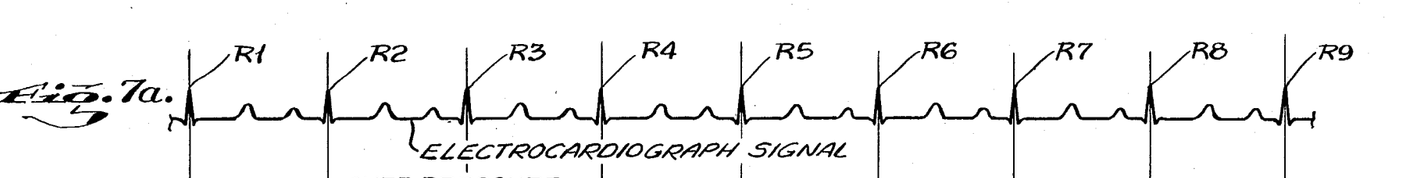
FIGS. 7a and 7b illustrate the measurements of FIGS. 4a and 4b taken with a more slowly decreasing cuff pressure.
Figure 7B:
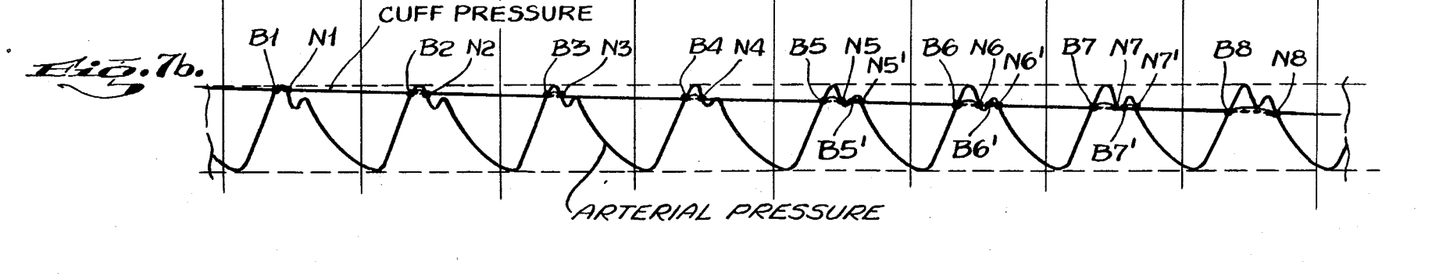
Figure 8:
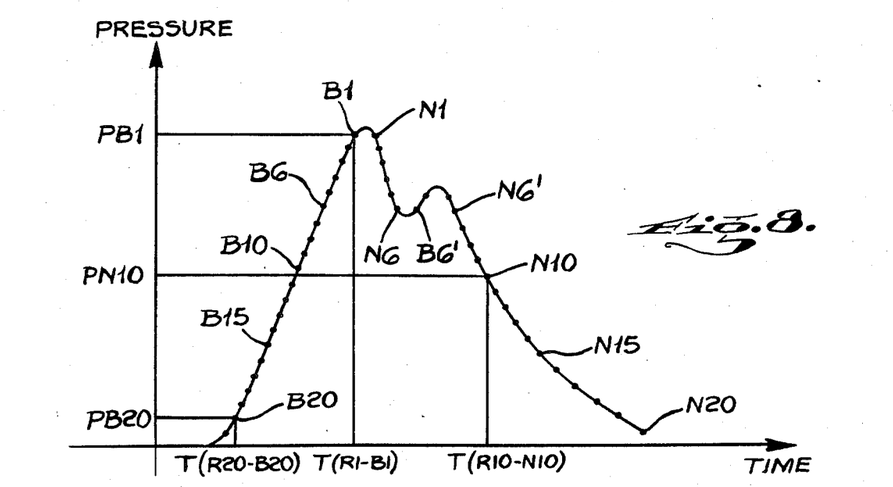
FIG. 8 illustrates the reproduced blood pressure waveform from the data points obtained in accordance with FIGS. 7a and 7b.

FIG. 7a and FIG. 7b illustrate substantially the same electrocardiograph signal and blood pressure waveform, respectively, as shown in FIG. 4a and FIG. 4b. In this procedure, the processor 50 (FIG. 3) has applied control signals to pressure generator 32 (FIG. 3) to release the pneumatic pressure in the cuff more gradually than was done for the measurments taken in connection with FIG. 4b. Thus, as the cuff pressure decreases, a larger number of samples are taken during the measurement portion of the examination. The samples are retained in the memory of the processor 50 until the processor 50 determines that the last transition point has occurred in the manner set forth above. The sampled data can be operated on by the algorithms as described above in connection with FIG. 4b. Furthermore, as illustrated in FIG. 8, the increased number of samples provides a more detailed representation of the pressure waveform. The additional data points (B9-B21 and N9-N20) in FIG. 8 represent samples taken if FIGS. 7a and 7b were to be extended.

Although a more slowly decreasing cuff pressure requires a longer duration for the procedure, it is particularly advantageous that the apparatus and method described is synchronized with the heart rate and can obtain one sample per heart beat. Thus, at a heart rate of 60 beats per minute, the waveform represented in FIG. 8 would have been obtained in approximately 20 seconds, with a small amount of additional time required to inflate the cuff above the expected systolic pressure and to deflate the cuff after reaching the diastolic pressure. In non-synchronized prior art methods the cuff pressure would be decreased intermittently and allowed to stabilize in order to assure that an accurate measurement is taken at each pressure level. The apparatus and method illustrated also have the advantage that the diastolic pressure is recognized by the absence of further transitions in the detected cuff pressure. Thus, if there are no transitions within a few heart beats (typically two or three), the cuff pressure can be rapidly deflated to allow the release of the venous blood pool and thus more quickly reduce the discomfort to the patient.

Figures 9A, 9B:
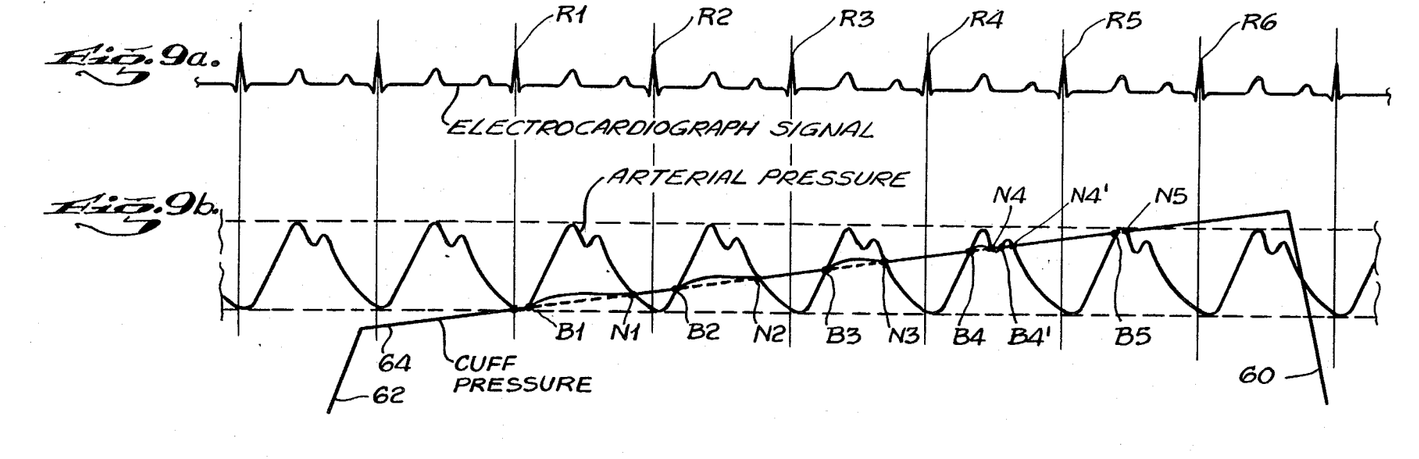
FIGS. 9a and 9b illustrate the measurment of blood pressure using an increasing cuff pressure.

The apparatus and method described above also have the further advantage that there is no longer any requirement to inflate the cuff pressure above the systolic blood pressure. Although described above in connection with a gradually decreasing cuff pressure, the instant invention can also be used with increasing cuff pressure as illustrated in FIGS. 9a and 9b. Once the processor 50 (FIG. 3) determines that the transducer 34 is no longer detecting any momentary pressure increases above the expected cuff pressure, the cuff 30 can be rapidly deflated to avoid any further discomfort to the patient 10. The rapid deflation is illustrated by transition line 60 in the cuff pressure. In order to further decrease the amount of time in which venous pooling occurs, the cuff pressure can be initially increased quite rapidly to a point below the expected diastolic pressure as illustrated by transition line 62. Then, the cuff pressure is gradually increased at the known, constant rate, illustrated as line 64 on the cuff pressure waveform, to take the samples as described above in connection with decreasing cuff pressure.

Figure 10A:
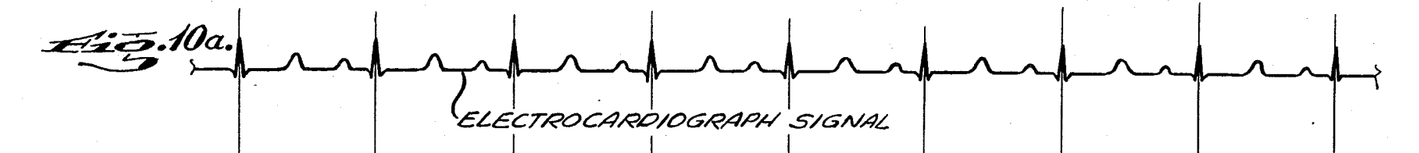
FIGS. 10a and 10b illustrate the measurement of FIGS. 9a and 9b with compensation for an initial cuff pressure which is too great.
Figure 10B:
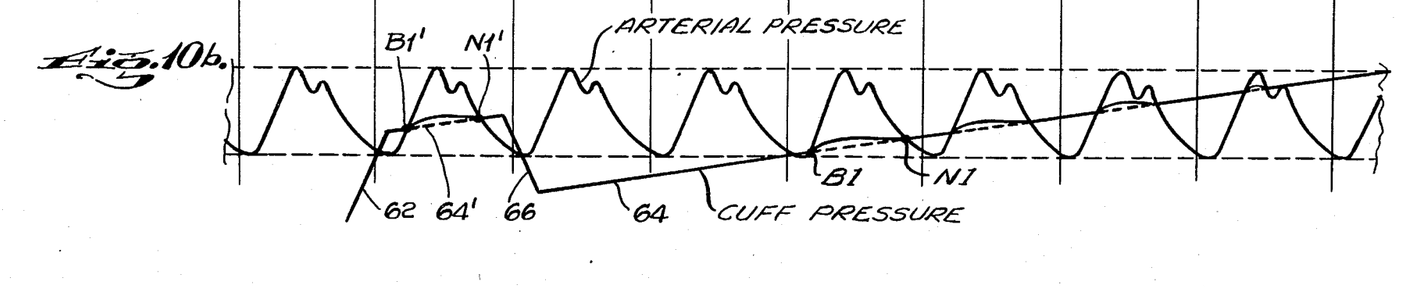

If, as illustrated in FIGS. 10a and 10b, the first detected transitions, B1' and N1' occur before at least one heart cycle occurs without a transition, the cuff pressure may have been inflated above the diastolic blood pressure, as illustrated by portion 64' of the graph. If this event occurs, the cuff pressure can be rapidly decreased by a small amount (e.g., 20 or 30 torr), as illustrated by portion 66 of the graph. The cuff pressure is then inflated, as before. As long as at least one heart cycle occurs before the occurrence of pressure transitions, B1 and N1, the measurement cycle can continue along pressure slope 64 since the measurement started with the cuff pressure below the diastolic blood pressure. Otherwise, the cycle is stopped and the starting pressure is again reduced still lower. The processor 50 (FIG. 3) is programmed to monitor the output of the analog-to-digital converter 37 (FIG. 3) and halt the measurement process if a transition is detected before at least two R-waves occur. If the transition is detected, a command is sent to the pressure generator 32 to lower the pressure, followed by a command to increase the pressure at a steady rate.

Figure 11A:
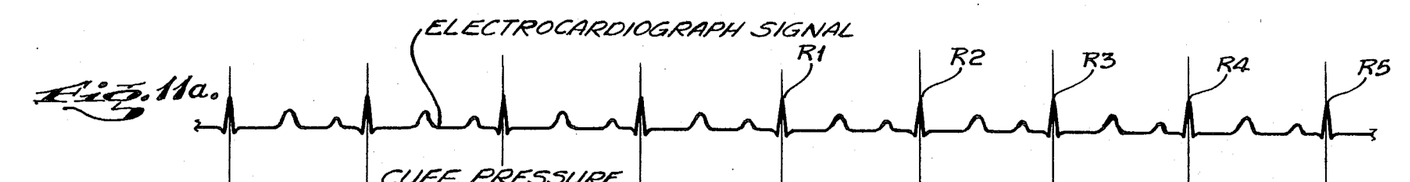
FIGS. 11a and 11b illustrate the measurement of blood pressure using a step-wise decreasing cuff pressure.
Figure 11B:
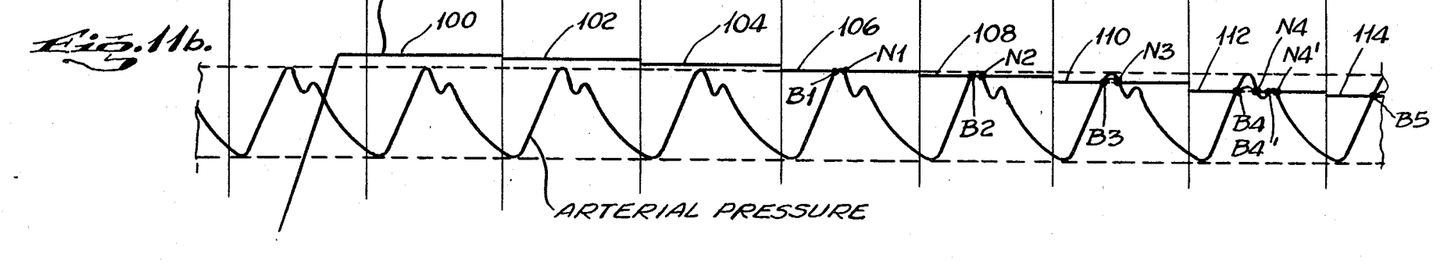

In the previously described methods the processor 50 send commands to the pressure generator 30 to increase or decrease the pressure at a known steady rate. Thus, as illustrated in FIGS. 4b, 7b, 9b and 10b, the cuff pressure increases or decreases linearly. FIGS. 11a and 11b illustrate a further embodiment of the apparatus and method in which the cuff pressure, illustrated by graph portions 100–114, is decreased in finite steps rather than linearly, as described above. The processor 50 transmits discrete commands to the pressure generator 30 to decrease the pressure in small steps. The amount of decrease at each step is determined by the accuracy of the measurements desired. Typically, the pressure would be decreased on each occurrence of the R-wave in order to assure that the pressure is stabilized prior to the occurrence of the systolic portion of the pressure wave, which typically occurs approximately in the middle of a heart cycle. Thus, the complexity of the internal calculations performed by the processor 50 is reduced since the cuff pressure is constant during each heart cycle and the expected cuff pressure does not have to be calculated. If further assurance of pressure stability is required, although not illustrated, each pressure step can last for two or more heart cycles, with the measurements being taken in the latter heart cycles. However, since the changes in pressure are synchronized with the heart rate, the cuff pressure will typically be changed every cardiac cycle, thus keeping the duration of measurements shorter.

Figure 12A:
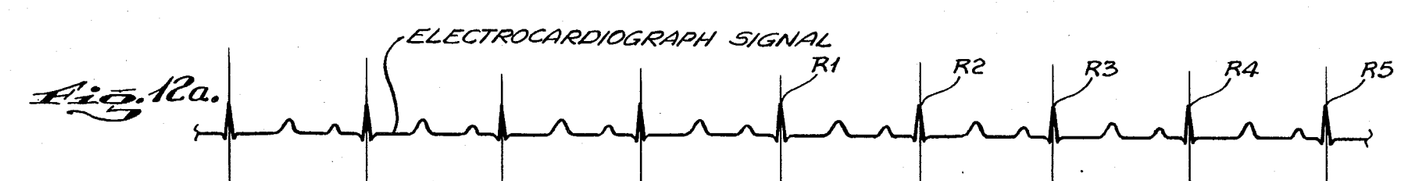
FIGS. 12a and 12b illustrate the measurement of blood pressure using a step-wise increasing cuff pressure.
Figure 12B:
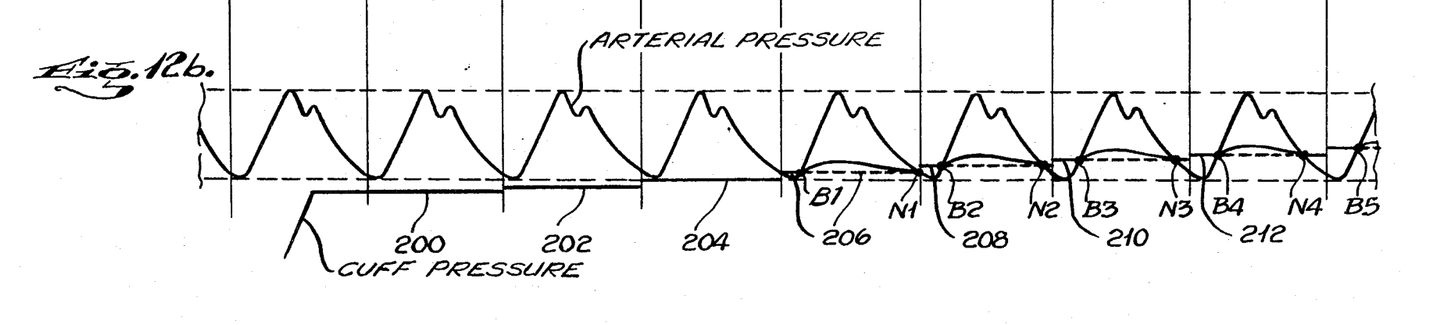

The step-wise method of varying pressure can also be used with increasing cuff pressure as illustrated in FIGS. 12a and 12b wherein graph portions 200–212 designate each step in the pressure increase. Again, the pressure increases are typically initiated at the occurrence of each R-wave in the heart cycle. Furthermore, although not illustrated, each step can last for multiple heart cycles, if desired.

The apparatus and method described above can be advantageously used in a fully automated patient monitoring system. The processor 50 (FIG. 3) can be programmed to perform one of the measurement sequences described above on a periodic basis without any requirement for manual intervention. Thus, the processor 50 can determine whether the patient's blood pressure has increased above or decreased below a range of acceptable values, and sound an alarm to alert the physician or nurse on duty. Among the advantageous uses for the apparatus and method are the monitoring of patients for post-surgical shock or unexpected reactions to drug therapy.

Improved Cuff For Use With Calibrated Arterial Pressure Measurement Device

As set forth above, Applicant's invention can be used with a standard arterial pressure measurement cuff. The information obtained using Applicant's invention is more expensive and more accurate than was previously available using prior art methods. The accuracy of the present invention can be further increased by using a new and improved occlusive cuff described hereinafter.

Figure 13:
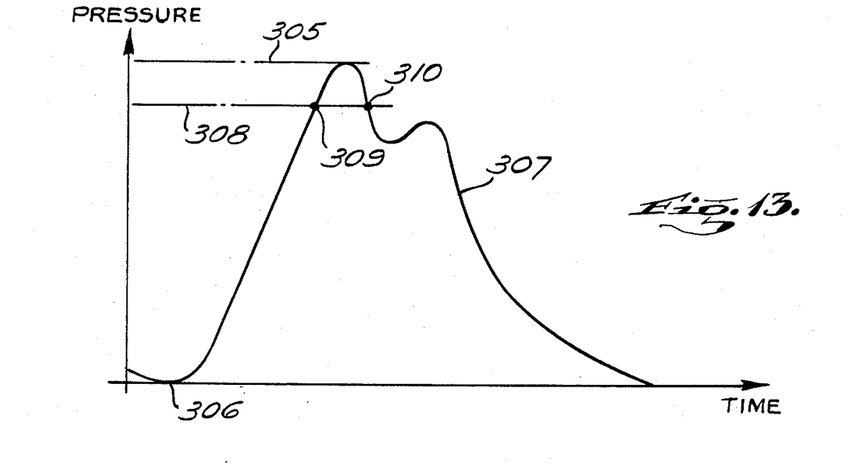
FIG. 13 illustrates the relationship between the cuff pressure and the arterial blood pressure during one heart cycle.

FIG. 13 depicts the relationship between the arterial pressure 307, wherein the systolic pressure level is designated as 305, the diastolic pressure level is designated as 306, and the cuff pressure level is designated as 308. It is assumed, for proper operation of the cuff, that the arterial pressure 307 will be able to overcome the occlusive cuff pressure 308 at the point 309. At that point, the arterial blood will flow from the proximal to the distal portion of the segment of the artery under the cuff in the time from point 309 to point 310, when the arterial pressure 307 again falls below the cuff pressure 308.

Figure 14:
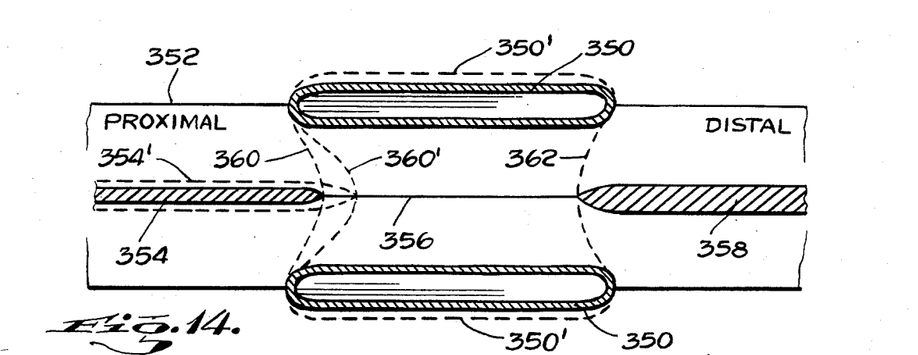
FIG. 14 is a partial cross-sectional view of an upper arm which illustrates the relationship between the occlusive cuff and the brachial artery.

A description of the apparatus and method above assumed the ideal operation of the artery and the measurement cuff. FIG. 14 is a partial cross-sectional view of a patient's arm with a cuff applied which more clearly illustrates the actual occurrence above the systolic blood pressure level. The cuff 350 surrounds the arm 352. The pressure of the cuff 350 is transmitted by the tissues of the arm 352 to the brachial artery illustrated in a proximal segment as 354, in a distal segment as 358 and in a collapsed middle segment as 356. The profile of the pressure transmitted by the tissues is graphically illustrated by dashed lines 360 and 362. Although ideally the middle segment 356 remains collapsed so long as the cuff pressure is greater than the systolic blood pressure, in actuality, the proximal segment of the artery 354 begins to expand during each cardiac cycle as a result of the arterial blood pressure compliance. The variation of the diameter of the proximal segment of the artery 354 as a result of the pressure compliance is illustrated by the second set of dashed lines 354'. As the proximal segment of the artery 354 expands, the pressure profile 360 in the tissues shifts to pressure profile 360', illustrated by dashed lines. The shift in the pressure profile 360' results in the reflection of a pressure pulse into the cuff 350 which expands slightly as illustrated by dashed lines 350'. This slight increase in pressure can be detected by the apparatus even in the suprasystolic range and can result in a false indication that the bolus of blood has passed although the cuff pressure is above the systolic pressure.

The foregoing can be illustrated as follows. Assume that the volume of air in the inflated cuff is 150 ml. Assume further that the collapse of the middle segment of the artery 356 causes a 5 ml decrease in the volume of the tissues of the arm beneath the cuff 350. This decrease in volume will be reflected as 5/150 decrease in the pressure in the cuff 350. Similarly, the expansion of the middle segment of the artery 356 will cause a corresponding increase in the cuff pressure which is detectable. Therefore, assuming the mean pressure level being measured is 100 torr, the pressure will vary approximately 3.3 percent with each heartbeat as the middle segment of the artery 356 expands and collapses beneath the cuff 350. This can result in minor erroneous measurements of the blood pressure since the same sensing transducer is measuring the cuff pressure and is also sensing the changes in cuff pressure. Furthermore, as set forth above, although the middle segment of the artery 356 may not expand sufficiently to allow the bolus of blood to pass beneath the cuff 350, the partial expansion can be detected by a transducer 34 (FIG. 3) as a false reading.

Although the percentage error in the measurements can be reduced by increasing the volume of air in the cuff, there would be a corresponding reduction in the sensitivity of the transducer to the pressure increases caused by the blood flow.

Figure 15:
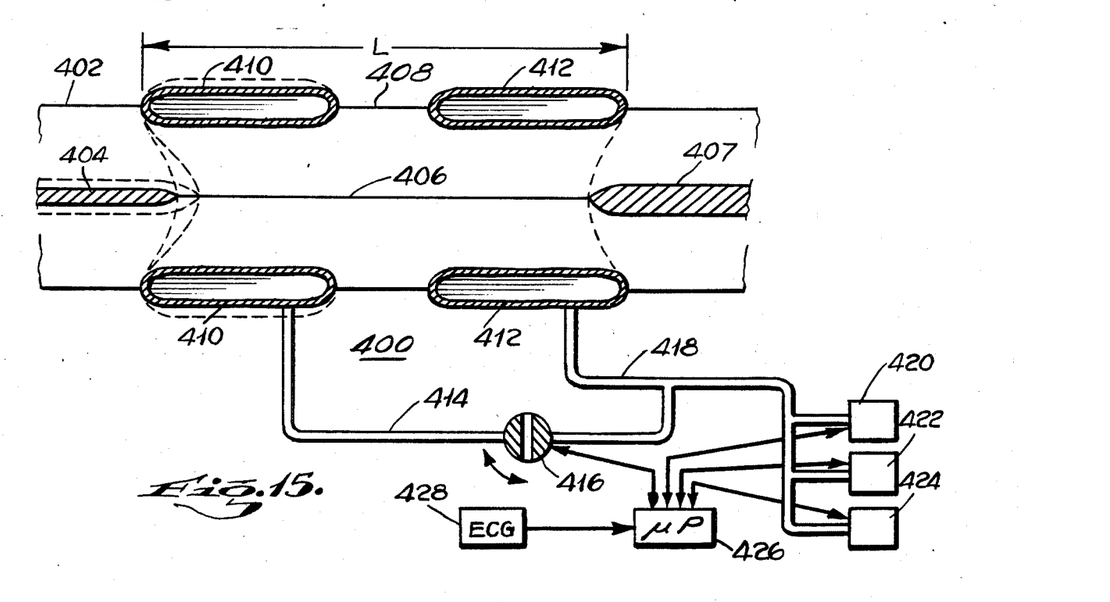
FIG. 15 illustrates a preferred embodiment of a pressure cuff and measuring system used to increase the accuracy of the blood pressure measurement.

FIG. 15 illustrates a modified cuff apparatus 400 which increases the accuracy of the pressure measurements. Instead of using one bladder to occlude the brachial artery (comprising a proximal segment 404, a collapsed segment 406 and a distal segment 407, in the arm 402) and to perform the measurements, a composite cuff 400 comprising an occlusive bladder 410, connected by a compliant spacing material 408 with a sensing bladder 412, is used. The spacing material 408 can be foam or other elastic material.

The occlusive bladder 410 is typically placed on the proximal portion of the upper arm, with sensing bladder 412 located distally from it. The occlusive bladder 410 has a pneumatic connection 414 to a valve 416. The sensing bladder 412 has a pneumatic connection 418 which is interconnected to the other side of the valve 416 and to a pump or other pneumatic source 420, a pressure transducer 422, and a bleeder valve 424. The bleeder valve 424 is typically part of the pump 420. The valve 416 can be an electrically-controlled rotational valve which is fully open in one position and is fully closed when rotated 90 degrees either direction from the fully open position. Other electrically-operated valves could be used for valve 416. In FIG. 15, the valve 416 is illustrated in the fully closed position. The valve 416, the pump 420, the transducer 422 and the bleeder valve 424 are connected to and controlled by the microprocessor 426. The microprocessor 426 is also electrically connected to the electrocardiograph equipment 428. Thus, the microprocessor 426 controls the changes in the applied pressure and monitors the detected pressure in synchronization with the R-wave of the electrocardiograph signal detected by the electrocardiograph equipment 428.

The apparatus operates by opening the valve 416 such that the pneumatic tube 414 is pneumatically connected to the pneumatic tube 418 and thus to the pump 420. The pressure pump 420 is actuated to inflate bladders 410 and 412 until the pressures in both bladders are equalized and are greater than the expected systolic blood pressure. At this point, the valve 416 is closed. With the valve 416 closed, the transducer 422 is pneumatically connected only to the sensing bladder 412. Thus, although the increase in the arterial pressure in the artery 404 with each heart beat may cause the collapsed segment 406 of the artery to partially expand and thus cause transient increases in the pressure in the occlusive bladder 410, as described above, and as illustrated in dashed lines, the pressure is not transmitted to the transducer 422 because of the isolation of the valve 416. Since both bladders have identical pressure levels, they act as one bladder of length L. The length of the occlusive bladder 410 is chosen to be sufficient to preclude the passage of a bolus of blood. Therefore, the sensing bladder 412 is isolated from any transient increase in blood pressure that is less than the pressure of the occlusive bladder 410. Thus, although the sensing bladder 412 is pneumatically connected to the transducer 422, the transient pressure increase is not detected by the transducer 422. However, when the blood pressure is sufficiently high to overcome the pressure of the occlusive bladder 410, the sensing bladder 412 will detect the pressure change caused by the passage of the bolus of blood beneath it through the previously collapsed arterial segment 406.

At each measurement step, the rotational valve 416 is rotated by 90 degrees to again pneumatically interconnect the occlusive bladder 410 and the sensing bladder 412. The bleeder valve 424 is momentarily operated to release a small amount of air in the two bladders. Since the two bladders 410, 412 are pneumatically interconnected, the pressure in each will be reduced to the same magnitude after a short amount of time because the pressure will equalize through the interconnection provided by rotational valve 416. The rotational valve 416 is then closed and another measurement is taken to determine whether a bolus of blood passes beneath the sensing bladder 412. If so, the times at which the pressure increase caused by the passage of the bolus of blood appears and disappears are measured as described before. Since the sensing bladder 412 is pneumatically isolated from the occlusive bladder 410 during the measurement portion of the cycle, no pressure transient is detected until the blood actually flows beneath the sensing bladder 412. The increase in pressure prior to the actual passage of the bolus of blood is not sensed by the sensing bladder 412. Thus, the times at which the blood begins to flow and stops flowing for each pressure level (e.g., points 309 and 310 in FIG. 13) can be more accurately determined than was previously done with the single bladder pressure cuff. The pressure to be recorded is the pressure of the sensing bladder 412 prior to the detected transient pressure.

The previous steps of alternately decreasing the pressure in the two bladders, isolating the occlusive bladder, and sensing the flow of blood in the sensing bladder, are repeated to obtain the data points according to the method described above in connection with the single bladder device.

The improved cuff 400 can also be used with increasing pressures. The rotational valve 416 is opened during each cycle and the pressure in the cuffs 410, 412 is increased by applying air from pressure pump 420. The rotational valve 416 remains open to allow the pressure in the two cuffs 410, 412 to equalize and is then closed. The measurements are taken as before. The steps are repeated at increasing cuff pressures until the systolic blood pressure is determined by the non-occurrence of a pressure transition during the measurement step.

Although the apparatus and method were described in connection with the brachial artery, the apparatus and method can be used in connection with other arteries with appropriate adjustments to the sizes of the cuffs and the magnitude of the pressures applied.

What is claimed is:

1. An apparatus for measuring arterial blood pressure and recreating the arterial blood pressure waveform throughout the cardiac cycle of a patient, comprising:
   an inflatable cuff;
   a source of selectively variable pneumatic pressure connected to said cuff to inflate and deflate said cuff;
   a pressure transducer connected such that it detects the magnitude of the pneumatic pressure applied to said cuff and provides a transducer output signal responsive to said magnitude, said transducer output signal including transitions corresponding to increases in the detected pressure magnitude at the beginning of arterial blood flow beneath said inflatable cuff during a cardiac cycle and transitions corresponding to decreases in the detected pressure at the end of arterial blood flow beneath said inflatable cuff during a cardiac cycle;
   an electrocardiographic means for sensing the electrical signals of the patient's heart and for providing an R-wave output signal responsive to the R-wave in said electrical signals; and
   a control means electrically connected to receive said transducer output signal and said R-wave output signal, which control means processes said output signals to calculate the elapsed times from the occurrence of the R-wave in a cardiac cycle to said transitions in said transducer output signal and to accumulate data corresponding to said calculated elapsed times and the magnitude of said pneumatic pressure for each cardiac cycle, and to provide output information corresponding to the magnitude of the blood pressure of the patient with respect to time within the cardiac cycle, said control means further providing control signals to said source of variable pneumatic pressure to control the rates of increase and decrease of said pneumatic pressure.

2. The apparatus of claim 1 wherein said control means is a programmable digital processor having a memory for storage of data.

3. The apparatus of claim 1 wherein said control signals control the rates of inflation and deflation of the cuff.

4. The apparatus of claim 1 wherein said output of said electrocardiographic means synchronizes said control means with the electrical activity of the patient's heart.

5. The apparatus of claim 1 where said control means accumulates said data at a plurality of pneumatic pressures and applies a numerical curve fitting algorithm to said accumulated data to calculate said output information, and recreate the blood pressure waveform with respect to the cardiac cycle.

6. The apparatus of claim 1 wherein said control means accumulates said data at a plurality of pneumatic pressures and calculates the ratio of the increase in arterial blood pressure with respect to time, said ratio corresponding to the contractility of the heart.

7. The apparatus of claim 1 wherein said control means accumulates said data at a plurality of pneumatic pressures and calculates the mean arterial blood pressure from said data.

8. The apparatus of claim 1 wherein said inflatable cuff comprises a occlusive bladder which can be inflated to collapse the artery beneath said bladder, and a sensing bladder, distal to said occlusive bladder, to detect pressure changes corresponding to the flow of blood in the artery beneath said sensing bladder.

9. The apparatus of claim 8 wherein said occlusive bladder and said sensing bladder are pneumatically interconnected by an electrically-controlled pneumatic valve, and wherein said occlusive bladder and said sensing bladder can be inflated and deflated to the same pressure and subsequently pneumatically isolated.

10. A method of measuring arterial blood pressure in a patient, comprising the steps of:
    applying a known varying pneumatic pressure to an inflatable cuff;
    measuring the magnitude of the pneumatic pressure in said cuff and providing a pressure output signal responsive to said magnitude, said pressure output signal including deviations detectable from said known varying applied pneumatic pressure, said deviations corresponding to the beginning and the end of arterial blood flow beneath the inflatable cuff;
    sensing the electrical signals of the patient's heart and providing an R-wave output signal responsive to the R-wave in said electrical signals;
    processing said pressure output signal and R-wave output signal to provide output information corresponding to the magnitude of the blood pressure waveform of the patient with respect to time in a cardiac cycle, said processing step including the steps of:
       calculating a first elapsed time from the occurrence of the R-wave to the pressure transition corresponding to the beginning of arterial blood flow;
       calculating a second elapsed time from the R-wave to the pressure transition corresponding to the end of arterial blood flow; and
       storing data corresponding to said first and second elapsed times and the corresponding known pneumatic pressures when the elapsed times were calculated; and
    repeating said measuring, sensing and processing steps at a plurality of known pneumatic pressures until there are no longer any detectable pressure deviations from the known varying applied pneumatic pressure.

11. The method of claim 10 further including the step of applying a curve fitting algorithm to the stored data to reproduce the pressure waveform corresponding to said stored data.

12. The method of claim 11 wherein the systolic and diastolic blood pressure correspond to the maximum and minimum points on said reproduced pressure waveform.

13. The method of claim 10 wherein the mean arterial blood pressure is calculated by applying an algorithm to said stored data.

14. An apparatus for measuring arterial blood pressure in a patient comprising:
   first means for detecting coincidence of the arterial blood pressure with expected pressure values;
   second means for detecting the occurrence of ventricular contractions of the heart muscle; and
   third means responsive to said first means and said second means for providing a reproduction of the arterial blood pressure waveform in a cardiac cycle.

15. The apparatus of 14 wherein said first means comprises:
   an inflatable occlusive cuff;
   a pressure transducer connected to said cuff, said transducer providing a signal output responsive to the pressure within said cuff; and
   a means for comparing said output of said transducer with said expected pressure values to provide signals corresponding to transitions of the cuff pressure from and to said expected values.

16. The apparatus of claim 15 wherein said third means generates data corresponding to the magnitude of the expected pressure values at the transitions and the times of occurrence of the transitions relative to the occurrence of the ventricular contractions, said data combinable to reproduce the pressure waveform.

17. An apparatus for measuring arterial blood pressure in a patient comprising:
   first means for successively detecting the occurrences of the arterial pressure in excess of a known, non-constant pressure value;
   second means for successively detecting the ventricular contractions of the heart muscle; and
   third means responsive to said first and second means for measuring successive time intervals between the beginnings of said ventricular contractions and the beginnings and ends of said occurrences of arterial pressure in excess of said known pressure values, said third means comprising:
      a means for recording data corresponding to said measured time intervals and said pressure values; and
      a means for analyzing said recorded data and thereby reproduce a representation of an arterial pressure waveform in a cardiac cycle corresponding to said recorded data.

18. An occlusive cuff for use in an arterial blood pressure measuring system, comprising:
   first and second pneumatically isolatable, mechanically interconnected inflatable bladders forming a single composite cuff for placement around an appendage so that said second bladder is located distally on said appendage with respect to said first bladder;
   means for varying the pneumatic pressure applied to said bladders so that said first and second bladders operate together to occlude an artery in said appendage beneath said bladders; and
   means for detecting transitions in the pneumatic pressure of said second bladder caused by blood flow in the artery beneath said first and second bladders when the arterial blood pressure exceeds the pneumatic pressure in said first and second bladders.

19. A method of measuring arterial blood pressure in a patient comprising the steps of:
   applying a known pneumatic pressure to a composite cuff comprising first and second inflatable bladders, thereby occluding an artery beneath said first and second bladders;
   pneumatically isolating said first bladder from said second bladder;
   detecting transitions in the pressure of said second bladder, thereby sensing arterial blood flow through said artery;
   detecting the occurrences of the ventricular contractions of the heart;
   measuring the time between said occurrences and said transitions in the pressure of said second bladder at a plurality of pressures;
   recording said measured time and said known pneumatic pressure;
   successively varying said pneumatic pressure and repeating said applying, isolating, detecting and recording steps; and
   reproducing the arterial pressure waveform from said recorded measured times and pressures.

20. A method of measuring the contractility of a patient's heart comprising the steps of:
   applying a known varying pneumatic pressure to an inflatable cuff;
   measuring the magnitude of the pneumatic pressure in said cuff and providing a pressure output signal responsive to said magnitude, said signal having transitions corresponding to the beginning and end of blood flow in an arterial segment beneath said cuff;
   sensing the electrical signals of the patient's heart and providing an R-wave output signal responsive to the R-wave in said electrical signals; and
   processing said pressure output signal to provide output information corresponding to the rate of increase in the arterial blood pressure with respect to time in a cardiac cycle, said rate of increase proportional to the contractility of the heart.

21. An occlusive cuff for use in an arterial blood pressure measuring system, comprising:
   first and second mechanically interconnected inflatable bladders forming a single composite cuff for placement around an appendage so that said second bladder is located distally on said appendage with respect to said first bladder;
   means for selectively applying pneumatic pressure to said bladders and releasing pneumatic pressure from said bladders;
   pneumatic switch means connected between said first and second bladders for selectively pneumatically interconnecting said bladders so that the same pneumatic pressure is applied to said bladders to thereby occlude an artery in said appendage beneath said first and second bladders and for selectively pneumatically isolating said bladders after applying said pressure so that pressure transitions in said first bladder are not pneumatically transferred to said second bladder; and
   pressure sensing means pneumatically connected to said second bladder for detecting transitions in the pneumatic pressure of said second bladder caused by blood flow in the artery beneath said first and second bladders when the arterial blood pressure exceeds the pneumatic pressure in said first and second bladders.

* * * * *

UNITED STATES PATENT AND TRADEMARK OFFICE
CERTIFICATE OF CORRECTION

PATENT NO. : 4,677,984

DATED : July 7, 1987

INVENTOR(S) : Bohumir Sramek

It is certified that error appears in the above-identified patent and that said Letters Patent is hereby corrected as shown below:

In Claim 20, at line 14, (Column 18, line 37), after "pressure output signal" insert --and R-wave output signal--.

Signed and Sealed this

Seventh Day of June, 1988

Attest:

DONALD J. QUIGG

Attesting Officer

Commissioner of Patents and Trademarks